United States Patent [19]

McDonald et al.

[11] Patent Number: 5,489,579
[45] Date of Patent: Feb. 6, 1996

[54] POTENTATION OF NMDA ANTAGONISTS

[75] Inventors: Ian A. McDonald, Loveland; Bruce M. Baron, Cincinnati, both of Ohio

[73] Assignee: Merrell Dow Pharmaceuticals Inc., Cincinnati, Ohio

[21] Appl. No.: 191,996

[22] Filed: Feb. 4, 1994

Related U.S. Application Data

[62] Division of Ser. No. 811,204, Dec. 20, 1991, Pat. No. 5,318,195.

[51] Int. Cl.$^6$ .................. A61K 31/675; A61K 31/60; A61K 31/62
[52] U.S. Cl. ............... 514/85; 514/159; 514/161
[58] Field of Search ................ 514/85, 159, 161

[56] References Cited

U.S. PATENT DOCUMENTS

| | | | |
|---|---|---|---|
| 2,608,508 | 8/1952 | Sprague | 514/192 |
| 4,960,786 | 10/1993 | Salituro et al. | 514/419 |
| 5,051,442 | 9/1991 | Salituro et al. | 514/419 |
| 5,095,009 | 3/1992 | Whitten et al. | 514/85 |

FOREIGN PATENT DOCUMENTS

| | | |
|---|---|---|
| 2100127 | 12/1982 | United Kingdom . |
| 9201093 | 2/1992 | WIPO . |

OTHER PUBLICATIONS

Brain Research Bulletin, vol. 28, pp. 244–238, Vecsei, et al. (1982).

*Primary Examiner*—Zohreh Fay
*Assistant Examiner*—K. Weddington
*Attorney, Agent, or Firm*—J. Michael Dixon

[57] ABSTRACT

The present invention is directed to a method for poteniating the therapeutic effects of selected NMDA antagonists.

4 Claims, No Drawings

POTENTATION OF NMDA ANTAGONISTS

This is a divisional of application Ser. No. 07/811,204, filed Dec. 20, 1991, which issued as U.S. Pat. No. 5,318,195 on Jun. 7, 1994.

The present invention is directed to a method for potentiating the therapeutic effects of a group of excitatory amino acid antagonists. Another aspect of the invention is directed to new pharmaceutical compositions useful for the treatment of conditions associated with excessive excitatory amino acid activity.

In accordance with the present invention, it has been discovered that probenecid will potentiate the activity of the following excitatory amino acid antagonists:

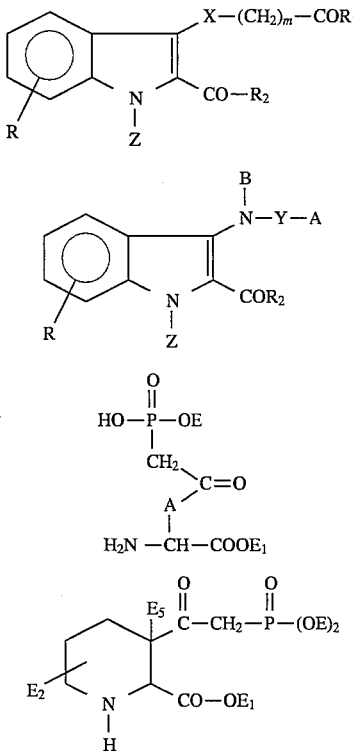

a) in the compounds of Formula Ia, X is represented by a linear $C_{1-4}$ alkylene, or S; m is an integer from 1–4; Z is represented by H, $C_{1-4}$ alkyl, phenyl, substituted phenyl, or an alkylphenyl substituent in which the phenyl ring may be optionally substituted; R is represented by hydrogen, halogen, $C_{1-4}$ alkyl, $C_{1-4}$ alkoxy, $CF_3$, $OCF_3$, OH, $NO_2$, or CN; $R_1$ and $R_2$ are each independently represented by —OH, —$OR_3$, —$NR_4R_5$, —$OCH_2OR_3$, or —O—$(CH_2)_n$—$NR_6R_7$, in which n is an integer from 1–4; $R_3$ is represented by $C_{1-4}$ alkyl, phenyl, substituted phenyl or an alkylphenyl substituent in which the phenyl ring may be optionally substituted; $R_4$ and $R_5$ are each independently represented by hydrogen or a $C_{1-4}$ alkyl; $R_6$ and $R_7$ are each independently represented by hydrogen or a $C_{1-4}$ alkyl, or $R_6$ and $R_7$ together with the adjacent nitrogen atom form a piperidino, morpholino, or pyrrolidino group with the proviso that if X is a $C_{1-4}$ alkylene, then m is O;

b) in the compounds of Formula Ib, R, Z, and $R_2$ are as above, B is represented by hydrogen, $C_1$–$C_4$ alkyl, optionally substituted alkylphenyl, or —$CH_2$—$COR_2$; Y is $SO_2$ or CO; and A is represented by phenyl, substituted phenyl, or C(O)D in which D is defined as $R_2$ above;

c) in the compounds of Formula Ic, E is represented by hydrogen, $C_{1-4}$ alkyl, or —$CF_3$; A is represented by a methylene or a trimethylene bridging group; and $E_1$ is represented by hydrogen, $C_{1-4}$ alkyl, cycloalkyl, trialkylamino, alkylphenyl, phenyl, or substituted phenyl;

d) in the compounds of Formula Id, E and $E_1$ are as above, $E_2$ is represented by hydrogen, $C_1$–$C_4$ alkyl, phenyl, alkylphenyl, or cyclohexylmethyl; and $E_5$ is represented by hydrogen, linear $C_1$–$C_4$ alkyl, or alkylphenyl; or a pharmaceutically acceptable salt of any of the compounds of Formulae Ia-d.

It has been discovered that probenecid will potentiate the therapeutic activity of the excitatory amino acid antagonists described by Formulae Ia-Id above (hereinafter the compounds). Thus the compounds will exhibit their therapeutic effects at lower doses and for longer periods in patients who are concurrently receiving probenecid. The mechanism by which probenecid potentiates their effects is not fully understood, however it is believed that probenecid decreases the rate at which the compounds are removed from the central nervous system as well as decreasing their rate of excretion by the kidneys. Probenecid increases the effective concentration of these compounds in both the CNS and in the systemic circulation.

As used in this application:

a) the terms "lower alkyl group and $C_1$–$C_4$ alkyl" refer to a branched or straight chained alkyl group containing from 1–4 carbon atoms, such as methyl, ethyl, n-propyl, isopropyl, n-butyl, isobutyl, etc;

b) the terms "lower alkoxy group and $C_1$–$C_4$ alkoxy" refer to a straight or branched alkoxy group containing from 1–4 carbon atoms, such as methoxy, ethoxy, n-propoxy, isopropoxy, n-butoxy, isobutoxy, etc.;

c) the term "cycloalkyl" refers to a cyclohexyl or a cyclopentyl group;

d) the term "substituted phenyl ring" refers to a phenyl ($C_6H_5$) which is substituted with up to 3 substituents, each substituent is independently selected from the group consisting of halogens, $C_1$–$C_4$ alkyl, $C_1$–$C_4$ alkoxy, $CF_3$, $OCF_3$, OH, and CN. These substituents may be the same or different and may be located at any of the ortho, meta, or para positions;

e) the term "alkylphenyl substituent" refers to the following structure —$(CH_2)_m$—$C_6H_5$, in which m is an integer from 1–3. This phenyl ring may be substituted in the manner described immediately above;

h) the term "pharmaceutically acceptable addition salt" refers to either a pharmaceutically acceptable acid addition salt or a pharmaceutically acceptable basic addition salt;

i) the term "halogen" refers to a fluorine, bromine or chlorine atom;

j) the term "trialkylamino" refers to

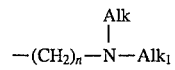

in which n is represented by an integer from 2–4 and Alk and $Alk_1$ are each independently represented by a $C_1$–$C_4$ alkyl; and k) the term "cyclohexylmethyl" refers to —$CH_2$—$C_6H_{12}$.

The expression "pharmaceutically acceptable basic addition salts" is intended to apply to any non-toxic organic or inorganic basic addition salts of the compounds represented by Formulae Ia-d or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline. Either the mono- or di-basic salts can be formed with those compounds.

The expression "pharmaceutically acceptable acid addition salts" is intended to apply to any non-toxic organic or inorganic acid addition salt of the base compounds represented by Formulae Ia-d or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxy-benzoic, phenylacetic, cinnamic, salicyclic, 2-phenoxy-benzoic, p-toluenesulfonic acid, and sulfonic acids such as methane sulfonic acid and 2-hydroxyethane sulfonic acid. Such salts can exist in either a hydrated or substantially anhydrous form.

The indole rings depicted in Formulae Ia and Ib are always substituted at positions 2 and 3, and may be optionally substituted at position 1. They may be further substituted as is indicated by the possible definitions for R. R may represent up to 3 additional substituents and these additional substituents may be located at any of positions 4, 5, 6, or 7. These substituents can be the same or different. In the compounds of Formulae Ia and Ib, $R_1$ and $R_2$ may be represented by the same substituents or differing substituents.

The compounds of Formula Ic exist as optical isomers. Any reference in this application to one of the compounds represented by Formula Ic is meant to encompass either a specific optical isomer or a mixture of optical isomers (unless it is expressly excluded). The specific optical isomers can be separated and recovered by techniques known in the art such as chromatography on chiral stationary phases or resolution via chiral salt formation and subsequent separation by selective crystallization. Alternatively utilization of a specific optical isomer as the starting material will produce the corresponding isomer as the final product.

As is indicated by the $E_2$ substituent in the compounds of formula Id, the piperidine ring may be further substituted at positions 4, 5, or 6. $E_2$ may optionally represent up to 2 non-hydrogen substituents. Only one non-hydrogen substituent should be located at any one position on the piperidine ring. If two non-hydrogen substituents are present, they may be the same or different. When $E_2$ is a non-hydrogen substituent, then this substituent may be either syn or anti relative to the phosphono substituent.

All of the compounds of Formula Id contain at least two (2) asymmetric centers and thus will exist as diasteriosmers. Any reference to these compounds as well as their intermediates should be construed as encompassing a racemic mixture, a specific optical isomer or a pair of enantiomers. The specific optical isomers can be synthesized as shown herein or can be recovered by techniques known in the art such as chromatography on chiral stationary phases, or resolution via chiral salt formation and subsequent separation by selective crystallization. HPLC ion exchange chromatography may be utilized to separate only the diastereomers.

Examination of Formula Id shows that the compounds contain a carbonyl function in the alkyl chain which is bonded to the 3-position of the piperidinyl ring. These compounds will exist in a state of tautomeric equilibrium in which the carbonyl function will participate in a keto-enol equilibrium reaction.

The compounds of Formula Ia in which X is represented by S is known in the art. The synthesis of these compounds, their use as excitatory amino acid antagonists, and methods for preparing pharmaceutical compositions from them are described in U.S. Pat. No. 5,051,442 which is hereby incorporated by reference. The preferred compounds of the 442' patent are those in which R is represented by a 4,6-dihalo substituent, X is S, m is 1, and Z is H. The most preferred compound is 3-[(carboxymethyl)thio]-2 -carboxy-4,6-dichloroindole.

Those compounds of Formula Ia in which X is a $C_{1-4}$ alkylene, and neither $R_1$ nor $R_2$ contain a heterocyclic ring are also known in the art. The use of the compounds as excitatory amino acid antagonists, and methods for preparing pharmaceutical compositions from them are described in U.S. Pat. No. 4,960,786 which is hereby incorporated by reference. The preferred compounds of the '786 patent are those in which R is represented by a 4,6-dihalo substituent, Z is H and X is ethylene. The most preferred compound is 3-(carboxyethyl)-2-carboxy-4,6-dichloroindole.

Those compounds of Formula Ia in which X is a $C_{1-4}$ alkylene, and one of $R_1$ or $R_2$ contain a heterocyclic ring are the subject of U.S. patent application Ser. No. 742,146 filed Aug. 1, 1991, having an effective filing date of Jul. 16, 1990, now allowed, which is hereby incorporated by reference. This application discloses methods for synthesizing these compounds, their use as excitatory amino acid antagonists, and methods for preparing pharmaceutical formulations from them. Preferred compounds are those in which R is represented by a 4,6-dihalo substituent.

The compounds of Formula Ib are the subject of U.S. patent application Ser. No. 07/608,457, filed Nov. 2, 1990, which is hereby incorporated by reference. This application describes methods for their synthesis, their use as excitatory amino acid antagonists and pharmaceutical formulations containing them. Preferred compounds are those in which R is a 4,6-dihalo substituent, B is alkyl, Z is hydrogen and A is phenyl. The most preferred compound is 3-[ (phenacyl)methylamino]-2-carboxy-4,6-dichloroindole.

The compounds of Formula Ic are known in the art and are described in European Patent Application No. 0 418 863 as well as its U.S. counterpart, U.S. patent application Ser. No. 553,431 filed Jul. 20, 1990, now allowed, which is hereby incorporated by reference. These applications describe methods for their synthesis, their use as excitatory amino acid antagonists and pharmaceutical formulations containing them. Preferred compounds include those in which A is methylene and E and $E_1$ are hydrogen. The most preferred compound is R-4-Oxo-5-phosphononorvaline.

The compounds of Formula Id are the subject of U.S. patent application Ser. No. 525,290 filed May 17, 1990 which is hereby incorporated by reference. This application discloses methods for their synthesis, their use as excitatory amino acid antagonists and pharmaceutical formulations containing them. Preferred compounds include those in which the stereochemistry is 2R,3S and in which $E_5$ is hydrogen or 4-alkyl. Preferred compounds include 3-(phosphonoacetyl)piperidine-2-carboxylic acid and 3-(phosphonoacetyl)piperidine-4-methyl-2-carboxylic acid.

Probenecid is also known in the art. It is available commercially from Merck Sharp and Dohme under the tradename Benemid® as well as being available from numerous other sources. Probenecid is a uricosuric agent and is utilized in the treatment of gout. Probenecid is a renal tubular transport blocking agent and has been utilized to increase plasma levels of penicillin. The pharmacology of probenicid is described in detail in the 45th Edition of the Physicians Desk Reference on page 1379.

As noted above, the compounds of Formulae Ia-Id are excitatory amino acid antagonists. They antagonize the effects which excitatory amino acids have upon the NMDA receptor complex. The compounds of Formula Ia and Ib preferentially bind to the strychnine-insensitive glycine binding site located on the NMDA receptor complex. The compounds of formula Ic and Id preferentially bind to the glutamate binding site located on the NMDA receptor complex. The compounds of formulae Ia-Id (hereinafter the compounds) are useful in the treatment of a number of disease states.

Ischemia, hypoglycemia, and trauma have been shown to raise extracellular concentrations of glutamate and aspartate to potentially neurotoxic levels. These antagonists will be neuroprotective in these and potentially other syndromes characterized by elevated glutamate and or aspartate concentrations. Thus the compounds are useful for preventing or minimizing the damage which nervous tissues contained within the CNS suffer upon exposure to either ischemic, hypoxic, traumatic or hypoglycemic conditions. Representative examples of such ischemic, hypoxic, or hypoglycemic conditions include strokes or cerebrovascular accidents, carbon monoxide poisoning, hyperinsulinemia, cardiac arrest, drownings, suffocation, reduction of neuronal damage following trauma to the brain or spinal cord, and neonatal anoxic trauma. The compounds should be administered to the patient within 24 hours of the onset of the hypoxic, ischemic, or hypoglycemic condition in order for the compounds to effectively minimize the CNS damage which the patient will experience.

The compounds exhibit anti-convulsant properties and are useful in the treatment of epilepsy. They are useful in the treatment of grand mal seizures, petit mal seizures, psychomotor seizures, and autonomic seizures. The compounds are also useful in the treatment of neurodegenerative diseases such as Huntington's disease, Alzheimer's disease, senile dementia, glutaric acidaemia type I, multi-infarct dementia, and neuronal damage associated with uncontrolled seizures. The administration of these compounds to a patient experiencing such a condition will serve to either prevent the patient from experiencing further neurodegeneration or it will decrease the rate at which the neurodegeneration occurs. As is apparent to those skilled in the art, the compounds will not correct any CNS damage that has already occurred as the result of either disease or a lack of oxygen or sugar. As used in this application, the term "treat" refers to the ability of the compounds to prevent further damage or delay the rate at which any further damage occurs. The compounds may also be utilized as anxiolytic agents and as analgesics. The therapeutic activity of these compounds is described in more detail in the United States patents and patent applications which were incorporated by reference above.

The compounds may be administered concurrently with probenecid in order to treat any of the diseases or conditions described above. The quantity of probenecid that is required to potentiate the therapeutic effects of the compounds can vary widely depending upon the particular compound of Formulae Ia-d being administered, the patient, and the presence of other underlying disease states within the patient, etc. Typically though, the probenecid may be administered at a dosage of from 0.5-3 g/day. Repetitive daily administration may be desirable and will vary according to the conditions outlined above. The probenecid will typically be administered from 2-4 times daily.

The dosage range at which the compounds of Formulae Ia-d exhibit their effects can vary widely depending upon the particular disease being treated, the severity of the patient's disease, the patient, the particular compound being administered, the route of administration, and the presence of other underlying disease states within the patient, etc. The dosage range at which the compounds of Formula Ia-d exhibit their antagonistic effect is presented below in Table I.

TABLE I

| COMPOUNDS | DOSAGE RANGE (Mg/Kg-day) |
| --- | --- |
| Ia | 0.1–50 |
| Ib | 0.1–50 |
| Ic | 1–500 |
| Id | 0.1–500 |

With the concurrent administration of probenecid, this dosage range may be adjusted lower by a factor of from 2- to 10-fold. Alternatively, the compounds may be administered at the same dosage range in order to obtain an enhanced effect due to the higher therapeutic concentrations obtained. The dosage frequency of the compounds can vary widely depending upon the condition or disease being treated. Repetitive daily administration may be desirable and will vary according to the conditions outlined above. For certain conditions such as stroke, it may be desirable to maintain a continuous IV infusion.

Probenecid is currently available commercially as tablets. The sodium salt of probenecid is readily water soluble and injectable dosage forms can be prepared from this salt using techniques well known to those skilled in the art.

The compounds may be administered by a variety of routes. They are effective if administered orally. The compounds may also be administered parenterally (i.e. subcutaneously, intravenously, intramuscularly, intraperitoneally, or intrathecally). The United States patents and patent applications discussed above teach methods for preparing pharmaceutical dosage forms containing the compounds.

The compounds of Formulae Ia-d and the probenecid may be administered as two different pharmaceutical dosage forms. Alternatively, in order to increase patient convenience, the compounds and the probencid may be compounded into a single pharmaceutical dosage form. These pharmaceutical compositions can be manufactured utilizing techniques known in the art. Typically an antagonistic amount of the compound and an effective amount of probenecid will be admixed with a pharmaceutically acceptable carrier.

For oral administration, the two medicaments can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations. In another embodiment, the two medicaments can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredients in an aqueous or non-aqueous pharmaceutically acceptable solvent which may also contain suspending agents, sweetening agents, flavoring agents, and preservative agents as are known in the art.

For parenteral administration the two medicaments may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the medicaments are being administered intrathecally, they may also be dissolved in cerebrospinal fluid as is known in the art.

As used in this application:

a) the term "patient" refers to warm blooded animals such as, for example, guinea pigs, mice, rats, cats, rabbits, dogs, monkeys, chimpanzees, and humans;

b) the term "treat" refers to the ability of the compounds to either relieve, alleviate, or slow the progression of the patient's disease;

c) the term "neurodegeneration" refers to a progressive death and disappearance of a population of nerve cells occurring in a manner characteristic of a particular disease state and leading to brain damage;

d) the phrase "concurrent administration" refers to administering the probenicid at an appropriate time so that it will potentiate the antagonistic effects of the compounds of Formula I. This may means simultaneous administration or administration at appropriate but different times. Establishing such a proper dosing schedule will be readily apparent to one skilled in the art.

The following Examples are being presented in order to further illustrate the invention but they should not be construed as limiting the scope of the invention in any manner.

EXAMPLE I

One method for evaluating the potential anti-epileptic activity of selected compounds is by their ability to inhibit sound induced seizures in audiogenic mice. DBA/2J audiogenic mice experience seizures when exposed to loud noises. Compounds which prevent this phenomenon are considered to be antiepilpetic agents.

Groups of 4 to 8 DBA/2J audiogenic mice were administered i.p. 4 to 5 doses ranging from 25 to 400 mg/kg of 3-[(phenacyl)methylamino]-2-carboxy-4,6-dichloroindole (hereinafter compound). Two hours after administration, they were placed individually in glass jars and exposed to a sound stimulus of 110 decibels for 30 seconds. Each mouse was observed during the sound exposure for signs of seizure activity. A graph was prepared based upon the dose administered and the percentage of animals protected at that dose. An $ED_{50}$ was calculated from the graph. In some mice the test was performed with the only modification being the addition of 100 mg/kg of probenecid IP. The following $ED_{50}$'s were obtained.

| TREATMENT | $ED_{50}$ (mg/kg) |
| --- | --- |
| Compound | 183.7 |
| Compound + Probenecid | 45.4 |

B) The protocol described above was repeated with minor variations with the compound 3-[(carbethoxymethyl)thio]-2-carbethoxy-4,6-dichloroindole. The test was conducted in the following manner.

Groups of DBA/2J audiogenic mice were administered i.p. 6 doses ranging from 25 to 400 mg/kg of 3-[(carboxymethyl)thio]-2-carboxy-4,6-dichloroindole (hereinafter compound). Five minutes after administration, they were placed individually in glass jars and exposed to a sound stimulus of 110 decibels for 30 seconds. Each mouse was observed during the sound exposure for signs of seizure activity. A graph was prepared based upon the dose administered and the percentage of animals protected at that dose. An $ED_{50}$ was calculated from the graph. The test was also performed in separate mice with the only modification being the addition of 100 mg/kg or 200 mg/kg of probenecid IP. The following $ED_{50}$'s were obtained.

| TREATMENT | $ED_{50}$ (mg/kg) |
| --- | --- |
| Compound | 149 |
| Compound + 100 mg/kg probenecid | 45.2 |
| Compound + 200 mg/kg | 11.0 |

EXAMPLE II

The intracerebroventricular administration of quinolinic acid induces clonic seizures in mice. If a compound can inhibit the development of these seizures, it is considered to possess anti-epileptic activity. This example demonstrates the manner in which probenecid potentiated the ability of R-4-Oxo-5-phosphononorvaline to inhibit the development of these seizures.

In this test, groups of 10 mice were pretreated intravenously with varying doses of R-4-Oxo-5-phosphononorvaline(hereinafter compound) ranging from 1 to 16 mg/kg. Five minutes later the mice were administered 7.7 micrograms of quinolinic acid intracerebroventricularly in a volume of 5 microliters of saline. The animals were observed for 15 minutes thereafter for signs of clonic seizures. A graph was prepared based upon the dose administered and the percentage of animals protected at that dose. An $ED_{50}$ was calculated from the graph. The test was then repeated in separate mice with the only modification being the addition of 100 mg/kg of probenecid IP. The following $ED_{50}$'s were obtained.

| TREATMENT | $ED_{50}$ (mg/kg) |
| --- | --- |
| Compound | 4.0 |
| Compound + Probenecid | 2.3 |

The protocol described above was repeated except that the compounds was administered intraperitoneally (dosage ranging from 0.5 to 32 mg/kg) and the pretreatment time was extended to 30 minutes. The following $ED_{50}$'s were obtained.

| TREATMENT | $ED_{50}$ (mg/kg) |
| --- | --- |
| Compound | 16.3 |
| Compound + Probenecid | 8.0 |

What is claimed is:

1. A pharmaceutical composition comprising: 1) a compound of the formula:

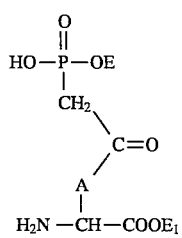

Ic in which E is represented by hydrogen, $C_{1-4}$ alkyl, or —$CF_3$; A is represented by a methylene or a trimethylene bridging group; and $E_1$ is represented by hydrogen, $C_{1-4}$ alkyl, cycloalkyl, trialkylamino, alkylphenyl, phenyl, or substituted phenyl, or a pharmaceutically acceptable salt thereof, which is present in an amount sufficient to antagonize the effects which excitatory amino acids have upon the NMDA receptor complex; 2) probenecid, which is present in an amount sufficient to potentiate said compound, and; 3) said compound and said probenecid are in admixture together with a pharmaceutical carrier.

2. A pharmaceutical composition according to claim 1 in which said compound is R-4-oxo-5-phosphononorvaline.

3. A method for antagonizing the effects of excitatory amino acids upon the NMDA receptor complex comprising administering to a patient in need thereof:

1) a compound of the formula:

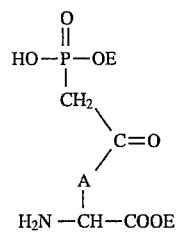

Ic in which E represented by hydrogen, $C_{1-4}$ alkyl, or —$CF_3$; A is represented by a methylene or a trimethylene bridging group; and $E_1$ is represented by hydrogen, $C_{1-4}$ alkyl, cycloalkyl, trialkylamino, alkylphenyl, phenyl, or substituted phenyl, or a pharmaceutically acceptable salt thereof, in an amount sufficient to antagonize the effects which excitatory amino acids have upon the NMDA receptor complex; and, 2) probenecid, in an amount sufficient to potentiate said antagonistic effects.

4. A method according to claim 3 in which said compound is R-4-oxo-5-phosphononorvaline.

* * * * *